(12) United States Patent
Amon

(10) Patent No.: US 10,004,592 B2
(45) Date of Patent: Jun. 26, 2018

(54) INTRAOCULAR LENS

(75) Inventor: Michael Amon, Vienna (AT)

(73) Assignee: Rayner Intraocular Lenses Limited, East Sussex (GB)

( * ) Notice: Subject to any disclaimer, the term of this patent is extended or adjusted under 35 U.S.C. 154(b) by 1 day.

(21) Appl. No.: 12/447,991

(22) PCT Filed: Nov. 26, 2007

(86) PCT No.: PCT/GB2007/004505
§ 371 (c)(1),
(2), (4) Date: Apr. 30, 2009

(87) PCT Pub. No.: WO2008/065362
PCT Pub. Date: Jun. 5, 2008

(65) Prior Publication Data
US 2010/0070030 A1 Mar. 18, 2010

(30) Foreign Application Priority Data

Nov. 27, 2006 (GB) .................................. 0623657.4

(51) Int. Cl.
*A61F 2/16* (2006.01)
(52) U.S. Cl.
CPC .... *A61F 2/1602* (2013.01); *A61F 2002/1681* (2013.01); *A61F 2002/1699* (2015.04)
(58) Field of Classification Search
USPC .................... 623/6.32, 6.34, 6.38, 6.43, 6.49
See application file for complete search history.

(56) References Cited

U.S. PATENT DOCUMENTS

| | | | | |
|---|---|---|---|---|
| 4,502,163 A | * | 3/1985 | Graham | 623/6.46 |
| 4,578,078 A | * | 3/1986 | Arkell | A61F 2/16 623/6.51 |
| 4,629,462 A | * | 12/1986 | Feaster | 623/6.51 |
| 4,706,666 A | * | 11/1987 | Sheets | 606/107 |
| 4,769,035 A | | 9/1988 | Kelman | |
| 4,813,953 A | * | 3/1989 | Sheets | A61F 2/1664 623/6.55 |
| 4,990,159 A | * | 2/1991 | Kraff | 623/6.49 |
| 4,995,879 A | * | 2/1991 | Dougherty | 623/6.38 |
| 5,201,762 A | * | 4/1993 | Hauber | 623/6.34 |
| 5,843,188 A | * | 12/1998 | McDonald | 128/898 |
| 2004/0230300 A1 | * | 11/2004 | Bandhauer et al. | 623/6.37 |

FOREIGN PATENT DOCUMENTS

| | | | | |
|---|---|---|---|---|
| EP | 0195881 | * | 1/1986 | A61F 2/16 |
| FR | 2581535 | * | 11/1986 | A61F 2/16 |
| WO | WO 2001/08605 A1 | * | 2/2001 | A61F 2/16 |

* cited by examiner

*Primary Examiner* — Leslie Lopez
(74) *Attorney, Agent, or Firm* — Saliwanchik, Lloyd & Eisenschenk

(57) ABSTRACT

An intraocular lens comprises an optic and two or more haptics, wherein the optic is convexo-concave, i.e. both faces are curved in the same sense with respect to the plane defined by the rim of the optic, wherein the haptics lie at an angle with respect to said plane and on the same side thereof as the optic's faces, and wherein each haptic has a smooth, undulating radially outer edge.

9 Claims, 2 Drawing Sheets

INTRAOCULAR LENS

CROSS REFERENCE TO A RELATED APPLICATION

Figure 1A:
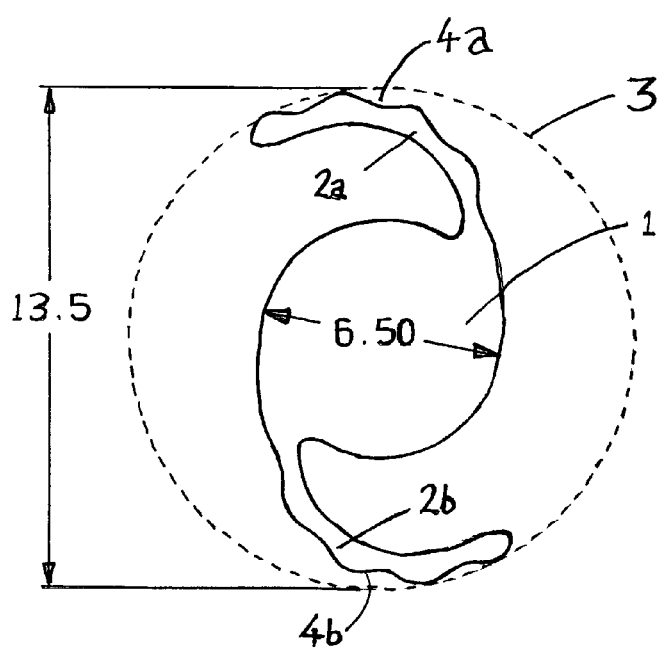

This application is a National Stage Application of International Application Number PCT/GB2007/004505, filed Nov. 26, 2007; which claims priority to Great Britain Application No. 0623657.4, filed Nov. 27, 2006; which are incorporated herein by reference in their entirety.

FIELD OF THE INVENTION

This invention relates to an intraocular lens, and in particular to a lens intended for use as supplementary to an existing such lens positioned within the lenticular capsule.

BACKGROUND OF THE INVENTION

Intraocular lenses generally comprise an optic and one or more haptics, and are typically placed in the lenticular capsule, to replace the natural lens. Many types of such intraocular lenses and configurations are known. Unsatisfactory placement or degradation of the lens, or degradation of the eye such that the lens is no longer especially effective, cannot readily be ameliorated by lens replacement.

It is also known to introduce a secondary lens in the sulcus. For example, a "multi-focal piggyback lens" is available from Zeiss under the name Acor®, and is intended for the simultaneous correction of residual ametropia and presbyopia. It comprises a convexo-concave optic, wherein both faces of the optic are curved in the same sense with respect to the plane defined by the rim of the optic, and haptics which lie in that plane. The distal ends of the haptics are intended to come into contact with the ciliary sulcus, typically at a diameter of 12.5-13.5 mm.

SUMMARY OF THE INVENTION

According to the present invention, an intraocular lens comprises an optic and two or more haptics, wherein the optic is convexo-concave, i.e. both faces are curved in the same sense with respect to the plane defined by the rim of the optic, wherein the haptics lie at an angle with respect to said plane and on the same side thereof as the optic faces, and wherein each haptic has a smooth, undulating radially outer edge.

The use of a lens according to the invention comprises its insertion into the ciliary sulcus of a subject who already has an intraocular lens within the lenticular capsule. The outer surface of the optic of the existing lens and the inner surface of the optic of the supplementary lens can have substantially the same curvature.

The angulation of the haptics is intended to minimise or prevent uveal contact with the lens, while the shaping of the haptics should prevent rotation, and their length should ensure good positioning within the sulcus, while minimising the pressure exerted by the haptics on the sulcus. The undulation may be continued along the length of the haptic, to the haptic/optic junction, in order to reduce the force of the lens, having a large haptic diameter on the sulcus.

DESCRIPTION OF PREFERRED EMBODIMENTS

One characteristic of a lens of the present invention is that the haptics lie at an angle to the plane defined by the rim of the optic. This angle is usually at least 5 or 8°, and typically no more than 15 or 20°. Most preferably, it is about 10°.

In a lens of the invention, it is intended that a radially outer edge of each haptic should come into contact with the sulcus. The length of the contact surface, or at least the distance between the points of contact, may be at least 1 mm, e.g. up to 4 mm or more, for a given size of sulcus, e.g. a diameter of 12.5-13.5 mm.

Another characteristic of the invention is that the radially outer edge of each haptic is smooth and undulating. The purpose of this shaping is both to minimise damage to the sulcus wall and to minimise rotation of the lens. Rotation may undesirably affect the corrective properties of the optic.

The maximum dimension of a lens according to the invention, which may be the distance between two opposed radially outer edges of opposed haptics, may be at least 10 or 12 mm, e.g. up to 14 or 15 mm. It will of course typically be determined having regard to the size of the patient's sulcus. Lenses of different sizes may be provided for a surgeon's use.

The optic may be essentially of a conventional type. It may be, for example, 5 to 8 mm in diameter.

Figure 1B:
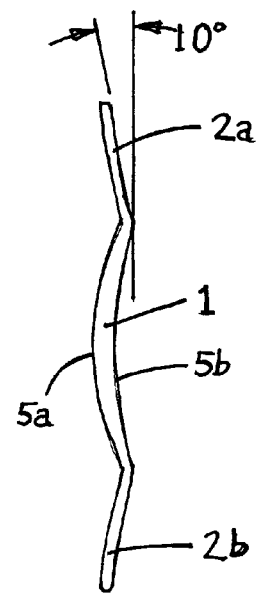
Figure 2:
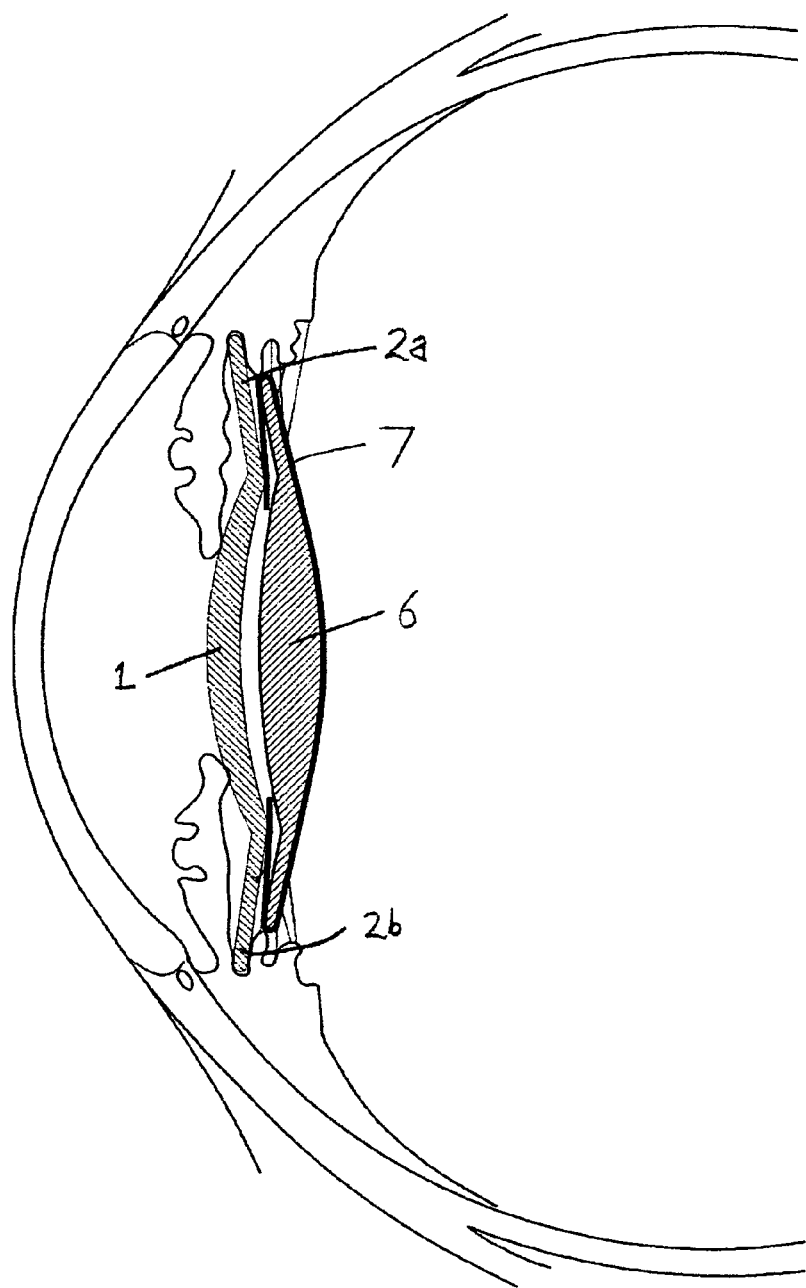

The invention will now be described by way of example only with reference to the accompanying drawings, in which:

FIG. 1 shows associated plan and side views of an intraocular lens that embodies the present invention; and FIG. 2 is a schematic view of part of the eye, showing two lenses (one embodying the invention) in position.

FIG. 1a shows a lens comprising an optic 1 (diameter 6.5 mm) and haptics 2a and 2b whose radially outer edges may be said to define the circle 3 shown in dotted outline, which is 13.5 mm in diameter. The radially outer edges 4a and 4b of the haptics are each undulating.

As shown in FIG. 1b, the optic is convexo-concave, its respective faces 5a and 5b each being curved in the same sense with respect to a plane defined by the rim of the optic. The haptics 2a and 2b are each essentially planar in this side view. The angle between the plane of each haptic and the plane defined by the rim of the optic is illustrated as being 10°.

FIG. 2 shows, in addition to a lens of the invention having an optic 1 and haptics 2a and 2b, a conventional intraocular lens 6 positioned within the capsular bag 7. It will be seen that the outer surface of the inner lens and the inner surface of the outer lens have essentially the same curvature. This is not essential, although it may be desirable to minimise the gap between the two. The supplementary lens, i.e. the lens according to the present invention, is positioned within the ciliary sulcus which, as will be evident from FIG. 2, has a somewhat greater diameter than the capsular bag. In practice, this lens will not usually touch the iris.

The invention claimed is:

1. A method of enhancing the sight of a subject who has a first intraocular lens within the lenticular capsule, wherein the method comprises inserting into the ciliary sulcus, after the first lens is already present within the lenticular capsule, a second intraocular lens that comprises an optic and two or more haptics, wherein the optic is convexo-concave, such that both faces are curved in the same sense with respect to the plane defined by the rim of the optic, wherein the haptics lie at a nonzero angle with respect to said plane and on the same side thereof as the optic's faces, wherein each haptic has a smooth, undulating radially outer edge that extends along the entire length of its respective haptic, wherein each haptic comprises multiple undulations arranged in an arcuate fashion on its radially outer edge, wherein each haptic comprises undulations over its entire radially outer edge, beginning at the optic, wherein each undulation comprises a peak and a trough, wherein each peak is curved, wherein each trough is curved, wherein each undulation occupies less than half the total length of the radially outer edge of the haptic, and wherein each haptic has a radially inner edge that extends along the entire length of its respective haptic and that is smooth and non-undulating over the entire radially inner edge, beginning at the optic.

2. The method according to claim 1, wherein the outer surface of the optic of the first lens and the inner surface of the optic of the second lens have substantially the same curvature.

3. The method according to claim 2, wherein each haptic is connected to the optic at one end and free at the other end.

4. The method according to claim 2, wherein the entire radially inner edge of each haptic is continuously curved, beginning at the optic.

5. The method according to claim 1, wherein the haptics lie at an angle of 5 to 20 degrees with respect to the plane defined by the rim of the optic.

6. The method according to claim 5, wherein each haptic is connected to the optic at one end and free at the other end.

7. The method according to claim 5, wherein the entire radially inner edge of each haptic is continuously curved, beginning at the optic.

8. The method according to claim 1, wherein each haptic is connected to the optic at one end and free at the other end.

9. The method according to claim 1, wherein the entire radially inner edge of each haptic is continuously curved, beginning at the optic.

\* \* \* \* \*